(12) United States Patent
Engel et al.

(10) Patent No.: US 8,383,605 B2
(45) Date of Patent: *Feb. 26, 2013

(54) USE OF ALKYLPHOSPHOCHOLINES IN COMBINATION WITH ANTIMETABOLITES FOR THE TREATMENT OF BENIGN AND MALIGNANT ONCOSES IN HUMANS AND MAMMALS

(75) Inventors: Jürgen Engel, Alzenau (DE); Eckhard Günther, Maintal (DE); Herbert Sindermann, Rodgau (DE); Babette Aicher, Frankfurt am Main (DE)

(73) Assignee: AEterna Zentaris GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/798,267

(22) Filed: Mar. 31, 2010

(65) Prior Publication Data
US 2011/0028421 A1   Feb. 3, 2011

Related U.S. Application Data

(63) Continuation-in-part of application No. 10/632,187, filed on Jul. 30, 2003.

(60) Provisional application No. 60/399,615, filed on Jul. 30, 2002.

(51) Int. Cl.
*A61K 31/70*   (2006.01)
*A61K 31/685*   (2006.01)
*C07C 9/02*   (2006.01)

(52) U.S. Cl. ............... 514/47; 514/49; 514/46; 514/77; 558/166; 558/190

(58) Field of Classification Search ............ 514/47, 514/49, 77, 43, 46; 558/166, 190
See application file for complete search history.

(56) References Cited

U.S. PATENT DOCUMENTS

| | | | |
|---|---|---|---|
| 5,219,866 A | 6/1993 | Schumacher et al. | |
| 5,942,639 A | 8/1999 | Engel et al. | |
| 6,093,704 A | 7/2000 | Nickel et al. | |
| 6,172,050 B1 | 1/2001 | Nossner et al. | |
| 6,538,029 B1 * | 3/2003 | Thompson et al. | 514/569 |
| 6,583,127 B1 | 6/2003 | Gajate et al. | |
| 6,696,428 B2 | 2/2004 | Nickel et al. | |
| 6,800,639 B2 | 10/2004 | Giles et al. | |
| 6,903,080 B2 | 6/2005 | Nossner et al. | |
| 2004/0147541 A1 * | 7/2004 | Lane et al. | 514/291 |
| 2005/0234017 A1 * | 10/2005 | Zeldis | 514/58 |
| 2007/0167408 A1 | 7/2007 | Perrissoud et al. | |
| 2011/0243933 A1 | 10/2011 | Poradosu et al. | |

FOREIGN PATENT DOCUMENTS

| | | |
|---|---|---|
| EP | 1 545 553 B1 | 7/2011 |
| WO | WO 99/37289 | 7/1999 |
| WO | WO 00/33917 | 6/2000 |
| WO | WO 02/066019 A2 | 8/2002 |
| WO | WO 03/055522 A1 | 7/2003 |
| WO | WO 2004012744 | 2/2004 |
| WO | WO 2005/000318 | 1/2005 |
| WO | WO 2006/081452 | 8/2006 |
| WO | WO 2011/123691 A1 | 10/2011 |

OTHER PUBLICATIONS

Georgieva et al. Cancer Letters 182(2) 163-174 (2002).*
ASCO Abstract 2006—Journal of Clinical Oncology, 2006 ASCO Annual Meeting Proceedings (Post-Meeting Edition)m vol. 24, No. 18S (Jun. 20 Supplement), 2006.
ASCO Abstract 2009—Journal of Clinical Oncology, 2009 ASCO Annual Meeting Proceedings (Post-Meeting Edition)m vol. 27, No. 15S (May 20 Supplement), 2009:4081.
Ayala, Gustavo, et al., Bortezomib-Mediated Inhibition of Steroid Receptor Coactivator-3 Degradation Leads to Activated Akt, Clin Cancer Res, Nov. 15, 2008, 7511-7518, 14(22).
Catley Laurence, et al., Alkyl Phospholipid Perifosine Induces Myeloid Hyperplasia in a Murine Myeloma Model, Experimental Hematology, 35 (2007), 1038-1046.
Chiarini, F., et al., The novel Akt Inhibitor, Perifosine, Induces Caspase-Dependent Apoptosis and Downregulates P-glycoprotein Expression in Multidrug-Resistant Human T-acute Leukemia Cells by a JNK-dependent Mechanism, Leukemia (2008) 22, 1106-1116.
Cirstea, Diana, et al., Dual Inhibition of Akt/Mammalian Target of Rapamycin Pathway by Nanoparticle Albumin-Bound-Rapamycin and Perifosine Induces Antitumor Activity in Multiple Myeloma, Mol Cancer Ther, Apr. 2010, 963-975, 9(4).
Crul, M., et al. Phase I and Pharmacological Study of Daily Oral Administration of Perifosine (D-21266) in Patients with Advanced Solid Tumours, European Journal of Cancer, 38 (2002), 1615-1621.
Dasmahapatra Girija P., et al., In vitro Combination Treatment with Perfosine and UCN-01 Demonstrates Synergism Against Prostate (PC-3) and Lung (A549) Eptithelial Adenocarcinoma Cell Lines, Clin Cancer Res, Aug. 1, 2004, 5242-5252, vol. 10.
David, E., et al., Perifosine Synergistically EnhancesTRAIL-Induced Myeloma Cell Apoptosis via Up-Regulation of Death Receptors, Clin Cancer Res 2008:14(16) Aug. 15, 2008, 5090-5098.
Dogan, S. Serdar, Ocular Side Effects Associated with Imatinib Mesylate and Perifosine for Gastrointestinal Stromal Tumor, Hematol Oncol. Clin N Am, 23 (2009) 109-114.

(Continued)

*Primary Examiner* — Shirley V Gembeh
(74) *Attorney, Agent, or Firm* — Goodwin Procter LLP

(57) ABSTRACT

The invention relates to the use of alkylphosphocholines in combination with antimetabolites for the treatment of multiple myeloma, colon cancer or renal cancer. Preferred alkylphosphocholines are described by the Formula II.

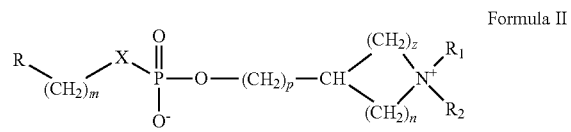

A particularly effective treatment includes administering a combination of perifosine and capecitabine.

9 Claims, No Drawings

OTHER PUBLICATIONS

Ellis, Matthew J., et al., "PIKing" the Winner for Phospatidylinositol 3-Kinase Inhibitors in ErbB2-Positive Breast Cancer: Let's Not "PTENed" It's Easy!, Clin Cancer Res, Oct. 1, 2007, 5661-5662, 13(19).

Engel, Jörg B., et al., Induction of Programmed Cell Death by Inhibition of AKT with the Alkylphosphochloine Perifosine in in Vitro Models of Platinum Sensitive and Resistant Ovarian Cancers, Arch Gynecol Obstet, doi:10.1007/s00404-010-1457-6; published online Apr. 20, 2010.

Engel, Jörg B., et al., Perifone Inhibits Growth of Human Experimental Endometrial Cancers by Blockade of AKT Phosphorylation, Eur J. Obstet. Gynecol (2008), doi:10.1016/j.ejogrb.2008.06.007.

Ernst, D. Scott, et al. Phase II Study of Perifosine in Previously Untreated Patients with Metastatic Melanoma, Investiational New Drugs, 23:569-576, 2005.

Festuccia, Claudio, et al., Akt Down-Modulation Induces Apoptosis of Human Prostate Cancer Cells and Synergizes with EGFR Tyrosine Kinase Inhibitors, The Prostate, 58:965-974 (2008).

Floryk, Daniel, et al., Perifosine Induces Differentiation and Cell Death in Prostate Cancer Cells, Cancer Letters, 266 (2008) 216-226.

Fomchenko, Elena I., et al., Mouse Models of Brain Tumors and Their Applications in Preclinical Trials, Clin Cancer Res., 2006:12(18) Sep. 15, 2006; 5288-5297.

Fu, Lei, et al., Perifosine Inhibits Mammalian Target of Rapamycin Signaling through Facilitating Degradation of Major Components in the mTOR Axis and Induces Autophagy, Cancer Res, Dec. 1, 2009, 8967-8976, 69(23).

Gajate, Consuelo, et al., Edelfosine and Perifosine Induce Selective Apoptosis in Multiple Myeloma by Recruitment of Death Receptors and Downstream Signaling Molecules into Lipids Rafts, Blood, Jan. 15, 2007, 711-719, vol. 109, No. 2.

Harvey, R. Donald, et al., P13 Kinase/AKT Pathway as a Therapeutic Target in Multiple Myeloma, Future Oncol., (2007) 3(6), 639-647.

Hideshima, Teru, et al., Perifosine, an Oral Bioactive Novel Alkylphospholipid, Inhibits Akt and Induces In Vitro and In Vivo Cytotoxicity in Human Multiple Myeloma Cells, Blood First Edition Paper, Jan. 17, 2006, 1-34, doi 10.1182/blood-2005-08-3434.

Hideshima, Teru, et al., Inhibition of Akt Induces Significant Downregulation of Survivin and Cytotoxicity in Human Multiple Myeloma Cells, British Journal of Haematology, 2007, 138, 783-791.

Huston, Alissa, et al., Targeting and Heat Shock Protein 90 Produces Synergistic Multiple Myeloma Cell Cytotoxicity in the Bone Marrow Microenvironment, Clin Cancer Res, Feb. 1, 2008, 865-874, 14(3).

Jendrossek, V., et al., Membrane Targeted Anticancer Drugs: Potent Inducers of Apoptosis and Putative Radiosensitisers, Curr. Med. Chem.—Anti-Cancer Agents, 2003, 3, 343-353.

Knowling, M., et al., a Phase II Study of Perifosine (D-21226) in Patients with Previously Untreated Metastatic or Locally Advanced Soft Tissue Sacoma: a National Cancer Institue of Canada Clinical Trials Group Trial, Invest New Drugs, (2006), 24:435-439.

Kodach, Liudmila L., vilacein Synergistically Increases 5-fluorouracil Cytotoxicity, Induces Apoptosis and Inhibits Akt-mediated Signal Transduciton in Human Colorectal Cancer Cells, Carcinogenesis, 2006, vol. 27, No. 3, 508-516.

Konstantinov, Spiro M., et al., BCR-ABL Influcences the Antileukaemic Efficacy of Alkylphosphocholines, British Journal of Haematology, 1999, 107, 365-374.

Konstantinov, Spiro M., et al., Human Urinary Bladder Carcinoma Cell Lines Respond to Treatment with Alkylphosphocholines, Cancer Letters, 1999, 144, 153-160.

Konstantinov, Spiro M., et al., Alkylphosphocholines: Effects on Human Leukemic Cell Lines and Normal Bone Marrow Cells, Int. J. Cancer, 1998, 77, 778-786.

Kumar, Anil, et al., the Alkylphospholipid Perifosine Induces Apoptosis and p21-Mediated Cell Cycle Arrest in Medulloblastoma, Mol Cancer Res, Nov. 2009, 1813-1821, 7(11).

Leighl, Natasha B., et al., A Phase 2 Study of Perifosine in Advanced or Metastatic Breast Cancer, Breast Cancer Res Treat (2008), 108:87-92.

Leleu, Xavier, et al., Targeting NF-κb in Waldenstrom Macroglobulinemia, Blood, May 15, 2008, 111(10), 5068-5077.

Li, X., et al., Enhancement of Antitumor Activity of the Anti-EGF Receptor Monoclonal Antibody Cetuximab/C225 by Perifosine in PTEN-deficient Cancer Cells, Onocogen, (2005), 1-11.

Lopiccolo, Jaclyn, et al., Targeting the P13K/Akt/mTOR Pathway: Effective Combinations and Clinical Considerations, Drug Resistance Updates, 11 (2008) 32-50.

Mitsiades, Constantin S., et al., Emerging Treatments for Multiple Myeloma: Beyond Immunomodulatory Drugs and Bortezomib, Seminars in Hematology, Apr. 2009, vol. 46, No. 2, 166-175.

Momota, Hiroyuki, et al., Perifosine Inhibits Multiple Signaling Pathways in Glial Progenitors and Cooperates With Temozolomide to Arrest Cell Proliferation in Gliomas In Vivo, Cancer Res, Aug. 15, 2005, 65(16), 7429-7435.

Nelson, EC, et al., Inhibition of Akt Pathways in the Treatment of Prostate Cancer, Prostate Cancer and Prostatic Diseases, (2007), 10, 331-339.

Nyåkern, Maria, et al., Synergistic Induction of Apoptosis in Human Leukemia T Cells by the Akt Inhibitor Perifosine and Etoposide Through Activation of Intrinsic and Fas-mediated Extrinsic Cell Death Pathways, Mol Cancer Ther, Jun. 2006, 5(6), 1559-1570.

Papa, V., et al., Proapoptotic Activity and Chemosensitizing Effect of the Novel Akt Inhibitor Perifosine in Acute Myelogenous Leukemia Cells, Leukemia, (2008), 22, 147-160.

Patel, Vyomesh, Perifosine, A Novel Alkylphospholipid, Induces p21WAF1 Expression in Squamous Carcinoma Cells Through a P53-independent Pathway, Leading to Loss in Cyclin-dependent Kinase Activity and Cell Cycle Arrest, Cancer Research, 62, 1401-1409, 2002.

Porta, Camillo, et al., Phosphatidylinositol-3-Kinase/Akt Signaling Pathway and Kidney Cancer, and the therapeutic Potential of Phosphatidylinositol-3-Kinase/Akt Inhibitors, The Journal of Urology, Dec. 2009, vol. 182, 2569-2577.

Rahmani, Mohamed, et al., Coadmininstration of Histone Deacetylase Inhibitors and Perifosine Synergistically Induces Apoptosis in Human Leukemia Cells Through Akt and ERK1/2 Inactivation and the Generation of Ceramide and Reactive Oxygen Species, Cancer Res, 2005, 2422-2432.

Tazaari, Pier Luigi, et al., Synergistic Proapoptotic Activity of Recombinant TRAIL Plus the Akt Inhibitor Perifosone in Acute Myelogenous Leukemia Cells, Cancer Res, Nov. 15, 2008, 68 (22), 9394-9403.

Ummersen et al., a Phase I Trial of Perifosine (NSC 639966) on a Loading Dose/Maintenance Dose Schedule in Patients with Advanced Cancer, Clinical Cancer Research, vol. 10, 7450-7456, Nov. 15, 2004.

Unger, Clemens, et al., First-Time-In-Man and Pharmacokinetic Study of Weekly Oral Perifosine in Patients with Solid Tumours, European Journal of Cancer, 46 (2010), 920-925.

Vinall, Ruth L., et al., Combination Treatment of Prostate Cancer Cell Lines with Bioactive Soy Isoflavones and Perifones Causes Increased Growth Arrest and/or Apoptosis, Clin Cancer Res, Oct. 15, 2007, 13(20), 6204-6216.

Vink, Stefan R., et al., Tumor and Normal Tissue Pharmacokinetics of Perifosine, An Oral Anti-Cancer Alkylphospholipid, Investigational New Drugs, 23, 2005, 279-286.

Vink, Stefan R., et al., Phase I and Pharmacokinetic Study of Combined Treatment With Perifosine and Radiation in Patients With Advanced Solid Tumours, Radiotherapy and Oncology, 80, 2006, 207-213.

Voltan, R., et al., Perifosine Plus Nutlin-3 Combination Shows a Synergistic Anti-Leukaemic Activity, British Journal of Haematology, 2010, 148(6), 957-961.

Younes, Hashem, et al., Targeting the Phosphatidylinositol 3-Kinase Pathway in Multiple Myeloma, Clin Cancer Res, Jul. 1, 2007, 13(13), 3771-3775.

Chou, Ting-Chao, Drug Combination Studies and Their Synergy Quantification Using the Chou-Talalay Method, Molecular Pharmacology and Chemistry Program, Memorial Sloan-Kettering Cancer Center, New York, NY USA. Cancer Reseach (2010), 70(2), 440-446.

Chou, Ting-Chao et al., Quantitative analysis of dose-effect relationships: the combined effects of multiple drugs or enyzme inhibitors, Lab. Pharmacol., Mem. Sloan-Kettering Cancer Cent., New York, NY, USA. Advances in Enzyme Regulation (1984), 22 27-55.

Page Brigitte, et al., A new fluorometric assay for cytotoxicity measurements in vitro, International Journal of Oncology 3: 473-476, 1993.

European Search Report dated Sep. 3, 2008.

Principe et al., Synergistic cytotoxic effect of aza-alkylphospholipids in association with chemotherapeutic drugs, J. Lipid Mediators Cell Signalling, 10. 1994, pp. 171-173.

Principe et al., Evaluation of combinations of antineoplastic ether phospholipids and chemotherapeutic drugs, Anti-Cancer Drugs, 3, 1992. pp. 577-587.

Ruiter et al., Alkyl-Lysophospholipids As Anticancer Agents and Enhancers of Radiation-Induced Apoptosis, Int. J, Radiation Oncology aiol. Phys.. 49(2), 2001, pp. 415-419.

Maly et el., Interference of new alkytphospholipid analogues with mitogenic signal transduction, Anti-Cancer Drug Design. 10. 1995. pp. 411-425.

Lohmeyer at al., Antitumor ether lipids and alkylphosphocholines, Drugs of the Future, 19 (11),1994, pp. 1021-1037.

Hilgard et al, D-21266, a New Heterocyclic Alkylphospholipid with Antitumour Activity, European Journal of Cancer, 33(3), 1997, pp. 442-446.

Thilo Sprub, Gunther Bernhardt, Helmut Schoenenberger and Jurgen Engel, Antitumor activity of miltefosine alone and after combination with platinum complexes on MXT mouse mammary carcinoma models; J Cancer Res Clin Oncol (1993) 119:142-149.

P. Hilgard, J. Stekar, T. Klenner, G. Nossner, B. Kutscher, and J. Engel; Heterocyclic Alkylphospholipids With an Improved Therapeutic Range; Advances in Experimental Medicine and Biology, United States (1996),157-164 (XP-002256712).

J. Stekar, P. Hilgard and T. Klenner; Opposite Effect of Miltefosine on the Antineoplastic Activity and Haematological Toxicity of Cyclophosphamide; Eur J Cancer, vol. 31A, No. 3, pp. 372-374,1995 (XP-002256713).

Milka C. Georgieva, Spiro M. Konstantinov, Margarit Topashka-Ancheva, Martin R Berger; Combination effects of alkylphosphocholines and gemcitabine in malignant and normal hematopoietic cells; Cancer Letters 182 (2002) 163-174 (XP-002256714).

D Berkovic, Eam Fleer, J Breass, J Pfortner, E Schleyer and W Hiddenmann; The influence of 1-B-D-arabinofuranosylcytosine on the metabolism of phosphatidylcholine in human leukemic HL 60 and Raji cells; Leukemia (1997) 11, 2079-2086 (XP-002256715).

Shoji M.; Raynor Rl.; Fleer E.A.; Eibl H.; Vogler W.R; Kuo J.F.; Effects of hexadecylphosphocholine on protein kinase C and TPA-induced differentiation of HL60 cells; Journal Article (Feb. 1991) vol. 26, No. 2, 145-149 (XP-002256716).

Aicher, B. et. al., Perifosine in Combination with Antimetabolites Induces Synergistic Effects on Cytotoxicity and Apoptosis in Human Colon, Multiple Myeloma, Breast, Renal , and Liver Tumor Cell Lines, Abstract #203—22nd EORTC-NCI-AACR Symposium on Molecular Targets and Cancer Therapeutics, Nov. 17, 2010.

Manfred E. Wolff, Burger's Medicinal Chemistry and Drug Discovery, 5th edition, vol. 1, 1995, pp. 975-997.

Goodman and Gilman, The Pharmacological Basis of Therapeutics, 9th Edition (1996) 1225-32.

Banker (Modem Pharmaceutics) Banker, G.S. et al, "Modem Pharmaceutics, 3ed.", Marcel Dekker, New York, 1996, pp. 451 and 596.

Awada et al. European J. of Cancer (2002) 38773-778.

Kasianenko et al, topical use of Miltex in patients with Breast Cancer's cutaneous manifestations, 1998:87. (2 pages) Abstract only.

Babette Aicher, et al., Perifosine in Combination with Antimetabolites Induces Synergistic Effects on Cytotoxicity and Apoptosis in Human Colon, Multiple Myeloma, Breast, Renal, and Liver Tumor Cells, Abstract 203 (Poster) 22nd EORTC-NCI-AACR Symposium on Molecular Targets and Cancer Therapeutics, Nov. 17, 2010.

Babette Aicher, et al., Perifosine in Combination with Antimetabolites Induces Synergistic Effects on Cytotoxicity and Apoptosis in Human Colon, Multiple Myeloma, Breast, Renal, and Liver Tumor Cells, (Abstract) 22nd EORTC-NCI-AACR Symposium on Molecular Targets and Cancer Therapeutics, Nov. 17, 2010.

Johanna Bendell, et al., Randomized Phase II Study of Perifosine in Combination With Capecitabine (P-CAP) vs. Capecitabine Plus Placebo (CAP) in Patients With Second or Third Line Metastatic Colon Cancer (MCRC): Updated Results (Poster), 2010 Gastrointestinal Cancers Symposium, held Jan. 22-24, 2010, Orlando FL.

Johanna Bendell, et al., Randomized Phase II Study of Perifosine in Combination With Capecitabine (P-CAP) vs. Capecitabine Plus Placebo (CAP) in Patients With Second or Third Line Metastatic Colon Cancer (MCRC): Updated Results, (Abstract), 2010 Gastrointestinal Cancers Symposium, held Jan. 22-24, 2010, Orlando FL.

R. Birch, et al., Perifosine (RX-0401)—An Active Agent in the Treatment of Patients with Advanced Sarcoma (Poster), 2007 ASCO Annual Meeting, held Jun. 1-5, 2007.

R. Birch, et al., Perifosine (P) as an active agent in the treatment of patients with advanced sarcoma, Journal of Clinical Oncology, 2007 ASCO Annual Meeting Proceedings Part I. vol. 25, No. 18S (Jun. 20 Supplement), 2007: 10059.

Rachel Midgley and David J Kerr, Capecitabine: have we got the dose right?, Nature Clinical Practice Oncology, pp. 17-24, Jan. 2009 vol. 6 No. 1.

D.C. Cho, et al. A phase II trial of perifosine in patients with advanced renal cell carcinoma (RCC) who have failed tyrosine kinase inhibitors (TKI), (Abstract), 2009 ASCO Annual Meeting, J Clin Oncol 27:15s, 2009 suppl; abstr 5101).

D.C. Cho, et al. A phase II trial of perifosine in patients with advanced renal cell carcinoma (RCC) who have failed tyrosine kinase inhibitors (TKI), (Poster), 2009 ASCO Annual Meeting held May 29-Jun. 2, 2009, Orlando, Florida.

Daniel Cho, et al., Inhibition of Glycogen Synthase Kinase 3β (GSK3β) Enhances the in Vitro Activity of the Akt Inhibitor Perifosine in Renal Cell Carcinoma (RCC) Cell Lines (Poster), 98th AACR Annual Meeting—held Apr. 14-18, 2007; Los Angeles, CA.

Daniel Cho, et al., Inhibition of Glycogen Synthase Kinase 3β (GSK3β) Enhances the In Vitro Activity of the Akt Inhibitor Perifosine in Renal Cell Carcinoma (RCC) Cell Lines (Abstract No. 1823), 98th AACR Annual Meeting—held Apr. 14-18, 2007; Los Angeles, CA.

Diana Cirstea, M.D., et al., Combination of Nab-Rapamycin and Perifosine Induces Synergistic Cytotoxicity and Antitumor Activity Via Autophagy and Apoptosis in Multiple Myeloma (MM) (Poster), American Society of Hematology (ASH) 50th Annual Meeting and Exposition, held Dec. 6-9, 2008; San Francisco, California.

Diana Cirstea, M.D., et al., Combination of Nab-Rapamycin and Perifosine Induces Synergistic Cytotoxicity and Antitumor Activity Via Autophagy and Apoptosis in Multiple Myeloma (MM) (Abstract), American Society of Hematology (ASH) 50th Annual Meeting and Exposition, held Dec. 6-9, 2008; San Francisco, California.

A. P. Conley, et al., A randomized phase II study of perifosine (P) plus imatinib for patients with imatinib-resistant gastrointestinal stromal tumor (GIST) (Abstract), 2009 Asco Annual Meeting, J Clin Oncol 27:15s, 2009 (suppl; abstr 10563), held May 29 through Jun. 2, 2009, Orlando, FL.

A. P. Conley, et al., A randomized phase Ii study of perifosine (P) plus imatinib for patients with imatinib-resistant gastrointestinal stromal tumor (GIST) (Poster), 2009 Asco Annual Meeting, held May 29 through Jun. 2, 2009, Orlando, FL.

Irene M. Ghobrial, et al., Phase II Trial of the Novel Oral Akt Inhibitor Perifosine in Relapsed and/or Refractory Waldenström Macroglobulinemia (Poster), 2007 ASH Annual Meeting, held Dec. 8-11, 2007, Atlanta, GA.

Irene M. Ghobrial, et al., Phase II Trial of Perifosine (KRX-0401) in Relapsed and/or Refractory Waldenström Macroglobulinemia: Preliminary Results (Abstract), Blood (ASH Annual Meeting Abstracts), Nov. 2007; 110: 4493.

F. A. Greco, et al., Safety and pharmacokinetic (PK) study of perifosine plus capecitabine (PCAP) in patients (pts) with refractory metastatic colorectal cancer (mCRC), J Clin Oncol 28, 2010 (suppl; abstr e14086), 2010 ASCO Annual Meeting.

Bryan Hennessy, et al., Perifosine accumulates preferentially in tumor tissues: Correlation between accumulation in tumor tissue and inhibition of cell proliferation and tumor growth (Poster), AACR- NCI-EORTC International Conference: Molecular Targets and Cancer Therapeutics—held Oct. 22-26, 2007; San Francisco, CA.

Bryan Hennessy, et al., Perifosine accumulates preferentially in tumor tissues: Correlation between intratumoral accumulation and inhibition of cell proliferation and tumor growth (Abstract) AACR Meeting Abstracts; 2007: C178, AACR-NCI-EORTC International. Conference: Molecular Targets and Cancer Therapeutics—held Oct. 22-26, 2007; San.Francisco, CA.

Hoff P., et al., O-0017. Subset Analysis of 5-Fu Refractory Patients From a Randomized PH II Study of Perifosine 1 Capecitabine (P-Cap) vs. Placebo 1 Capecitabine (Cap) In Patients With 2nd or 3rd Line Metastatic CRC (Abstract), 12th World Congress on Gastrointestinal Cancer, Barcelona, Spain, held Jun. 30-Jul. 2, 2010.

Paulo Hoff, et al., Subset Analysis of 5-Fu Refractory Patients From the Final Results of a Randomized Phase II Study of Perifosine in Combination With Capecitabine (P-Cap) vs. Placebo Plus Capecitabine (Cap) in Patients With Second or Third Line Metastatic Colorectal Cancer (mCRC) (Poster), 12th World Congress on Gastrointestinal Cancer, Barcelona, Spain, held Jun. 30-Jul. 2, 2010.

A. Huston, MD, et al., Combination of the Akt Inhibitor Perifosine with the Hsp90 Inhibitor 17-(dimethylaminoethylamino)-17-demethoxygeldanamycin (17-DMAG) has Synergistic Activity in Multiple Myeloma (Poster) 2005 ASH Annual Meeting, held Dec. 10-13, 2005; Atlanta, Georgia.

Alissa Huston, MD, et al., Combination of the AKT Inhibitor Perifosine with the HSP90 Inhibitor 17-(Dimethylaminoethylamino)-17-Demethoxygeldanamycin (17-DMAG) Has Synergistic Activity in Multiple Myeloma (MM) (Abstract) Blood (ASH Annual Meeting.Abstracts) 2005 106: Abstract 1592.

A. Huston, MD, et al., The Role of the Akt Inhibitor Perifosine in Migration and Adhesion in Multiple Myeloma A (Poster) 2005 ASH Annual Meeting, held Dec. 10-13, 2005; Atlanta, Georgia.

Alissa Huston, MD, et al., The Role of the AKT Inhibitor Perifosine in Migration and Adhesion in Multiple Myeloma (MM) (Abstract) Blood (ASH Annual Meeting Abstracts) 2005 106: Abstract 2509.

A. Huston, MD, et al., Proteomic Analysis Identifies Differences in Multiple Myeloma Cells Sensitive and Resistant to Akt Inhibition (Poster) 2005 ASH Annual Meeting held Dec. 10-13, 2005; Atlanta, Georgia.

Alissa Huston, MD, et al., Proteomic Analysis Identifies Differences in Multiple Myeloma (MM) Cells Sensitive and Resistant to AKT Inhibition (Abstract) Blood (ASH Annual Meeting Abstracts) 2005 106: Abstract 3402.

Andrzej Jakubowiak, et al., A Multiple Myeloma Research Consortium (MMRC) Multicenter Phase I Trial of Perifosine (Krx-0401) in Combination With Lenalidomide and Dexamethasone in Patients With Relapsed or Refractory Multiple Myeloma (MM): Updated Results Introduction (Poster) 2008 Blood (ASH Annual Meeting Abstracts) 2008 112: Abstract 3691.

Hyo Song Kim, et al., Evaluation of Anticancer Drug Sensitivity and Gene Expression Patterns of a Novel Akt Inhibitor, Perifosine in Gastric Cancer (Poster) 2011 AACR Annual Meeting held Apr. 2-6, 2011.

Tae Soo Kim et al., Presentation Title: Antitumor activity of novel Akt inhibitor, perifosine in gastric cancer cell lines (Abstract No. 1965) 2011 AACR Annual Meeting held Apr. 2-6, 2011.

Andrew Lassman, et al., Clinical and Molecular-Metabolic Phase II Trial of Perifosine for Recurrent/Progressive Malignant Glioma (Abstract) 12$^{th}$ Annual Meeting of the Society for Neurooncology held Nov. 15-18, 2007.

AB Lassman, et al., Phase II Trial of Perifosine for Recurrent Malignant Glioma (Poster) 12$^{th}$ Annual Meeting of the Society for Neurooncology held Nov. 15-18, 2007.

Zhijie Li, et al., Perifosine, as a single agent, inhibits neuroblastoma tumor cell growth in vitro and in vivo (Poster) 2009 AACR Annual Meeting held Apr. 18-22, 2009, Denver, CO.

Zhijie Li, et al, Perifosine, as a single agent, inhibits neuroblastoma tumor cell growth in in vitro and in vivo preclinical models (Abstract #3205) 2009 AACR Annual Meeting held Apr. 18-22, 2009, Denver, CO.

Zhijie Li, et al., Neuroblastoma tumors with different ALK mutations are sensitive to Perifosine (Poster) 101st Annual Meeting of the American Association for Cancer Research (AACR), Washington, DC. Apr. 21, 2010.

Zhijie Li, et al., Presentation Title: Neuroblastoma tumors with different ALK mutations are sensitive to Perifosine (Abstract No. 5248) 101st Annual Meeting of the American Association for Cancer Research (AACR), Washington, DC. Apr. 21, 2010.

Zhijie Li, et al., Perifosine, an Akt inhibitor, sensitizes Neuroblastoma to etoposide treatment (Poster) 2008.

Enrique Poradosu, et al., Perifosine selectively inhibits binding of Akt PH domain to PtdIns(3,4)P2 (Abstract #1645) 2007 AACR Annual Meeting held Apr. 14-18, 2007, Los Angeles, CA.

Enrique Poradosu, et al., Identification of Pharmacodynamic Markers for Effects of Perifosine (KRX0401) on the PI3K Pathway in vivo (Poster) 2005 AACR-NCI-EORTC International Conference on Molecular Targets and Cancer Therapeutics: Discovery, Biology, and Clinical Applications held Nov. 14-18, 2005.

Enrique Poradosu, et al., Identification of Pharmacodynamic Markers for Effects of Perifosine (KRX0401) on the PI3K Pathway in vivo (Abstract A194) 2005 AACR-NCI-EORTC International Conference on Molecular Targets and Cancer Therapeutics: Discovery, Biology, and Clinical Applications held Nov. 14-18, 2005.

Enrique Poradosu, Ph.D., Perifosine: An Akt Inhibitor in Clinical Trials, oral presentation at 2007 AACR Meeting.

Paul Richardson, MD, et al., Phase I/II of a Multicenter Trial of Perifosine (KRX-0401) + Bortezomib in Relapsed or Relapsed/Refractory Multiple Myeloma Patients Previously Relapsed From or Refractory to Bortezomib (Poster), Feb. 26, 2009.

Donald Richards, et al., Final Results of a Randomized Phase II Study of Perifosine in Combination With Capecitabine (P-CAP) vs. Placebo Plus Capecitabine (CAP) in Patients With Second or Third Line Metastatic Colorectal Cancer (mCRC) (Poster) 2010 ASCO Annual Meeting held Jun. 4-8, 2010—Chicago, IL; J Clin Oncol 28:15s, 2010 (suppl; abstr 3531).

Paul Richardson, MD, et al., Phase I/II Results of a Multicenter Trial of Perifosine (KRX-0401) + Bortezomib in Patients with Relapsed or Relapsed/Refractory Multiple Myeloma Who Were Previously Relapsed From or Refractory to Bortezomib; (Oral Session Novel Therapies for Myeloma and Related Disorders) Blood (ASH Annual Meeting Abstracts) 2008 112: Abstract 870.

Paul Richardson, Md, et al., A Multicenter Phase I/Ii Trial of Perifosine (Krx-0401) + Bortezomib in Relapsed or Relapsed/Refractory Multiple Myeloma Patients Previously Treated With Bortezomib: Phase I Results (Poster) Dec. 8, 2007 at the 49th Annual Meeting of the American Society of Hematology.

Paul Richardson, MD, et al., Phase I/II Report from a Multicenter Trial of Perifosine (Krx-0401) + Bortezomib in Patients with Relapsed or Relapsed/Refractory Multiple Myeloma Previously Treated with Bortezomib (Abstract) Blood (ASH Annual Meeting Abstracts) 2007 110: Abstract 1170.

Paul Richardson, MD, et al., A Phase I/II Study Evaluating the Safety and Efficacy of Perifosine + Bortezomib (+/-31 Dexamethasone) for Patients with Relapsed or Relapsed / Refractory Multiple Myeloma who were Previously Treated with Bortezomib (Power Point Presentation) 2008 ASH Meeting.

Paul Richardson, MD, et al., Perifosine in Combination with Bortezomib and Dexamethasone Extends Progression-Free Survival and Overall Survival in Relapsed/Refractory Multiple Myeloma Patients Previously Treated with Bortezombib: Updated Phase I/II Trial Results (Abstract No. 1869) (Poster Board 1-894) Blood (ASH Annual Meeting Abstracts) 2009, 114: Abstract 1869.

Paul Richardson, MD, et al., Perifosine Plus Bortezomib and Dexamethasone Extends Progression-Free Survival and Overall Survival in Relapsed / Refractory Multiple Myeloma Patients Previously Treated With Bortezomib: Updated Results of the Phase I/II Trial (Poster), 2009 ASH Annual Meeting held Dec. 5-8, 2009, New Orleans.

PG Richardson, et al., Phase I/II Trial of Perifosine + Bortezomib in Rel/Ref MM Patients Previously Treated with Bortezomib (Abstract), Feb. 26, 2009.

Alexandros S. Ardavanis, et al., Salvage Treatment with Single-agent Capecitabine in Patients with Heavily Pretreated Advanced Colorectal Cancer, Anticancer Research 26: 1669-1672 (2006).

N. J. Vogelzang, et al., Phase II Study of Perifosine in Metastatic RCC (Clear and Non-Clear) Progressing After One Prior Therapy (Rx) With a VEGF Receptor Inhibitor (Abstract), 2009 ASCO Genitourinary Cancers Symposium held Feb. 26-28, 2009, Orlando, Florida.

Nicholas J. Vogelzang, et al., Phase II Study of Perifosine in Metastatic Renal Cell Carcinoma (Clear and Non-Clear) Progressing After One Prior Therapy (Rx) With a VEGF Receptor Inhibitor (Poster) 2009 ASCO Genitourinary Cancers Symposium held Feb. 26-28, 2009, Orlando, Florida.

N. J. Vogelzang, et al., Phase II Study of Perifosine in Metastatic Renal Cell Carcinoma (RCC) Progressing After Prior Therapy (Rx) With a VEGF Receptor Inhibitor (Abstract) 2009 ASCO Annual Meeting, J Clin Oncol 27:15s, 2009 (suppl; abstr 5034).

Nicholas J. Vogelzang, et al., Phase II Study of Perifosine in Metastatic Renal Cell Carcinoma Progressing Either After One Prior Therapy (Rx) With a VEGF Receptor Inhibitor or a VEGF and an mTOr Inhibitor (Poster) 2009 ASCO Annual Meeting held May 29-Jun. 2, 2009, Orlando, Florida.

Ra Sasha Vukelja, et al., Randomized Phase II Study of Perifosine in Combination With Capecitabine vs. Capecitabine Alone in Patients With Second or Third Line Metastatic Colon Cancer (Poster) 2009 ASCO Annual Meeting held May 29-Jun. 2, 2009 in Orlando, Florida.

S. Vukelja, et al., Randomized phase II study of perifosine in combination with capecitabine versus capecitabine alone in patients with second- or third-line metastatic colon cancer, (Abstract No: 4081), 2009 ASCO Annual Meeting, J Clin Oncol 27:15s, 2009 (suppl; abstr 4081).

Apr. 2, 2012 Keryx Press Release.

Press release dated Apr. 8. 20 1 0, New York by Keryx Biopharmaceuticals, Inc.

Press release dated Feb. 3, 2010, New York by Keryx Biopharmaceuticals, Inc.

Press release dated Jan. 21, 2010. New York by Keryx Biopharmaceuticals, Inc.

Press release dated Jan. 25. 2010. New York by Keryx Biopharmaceuticals, Inc.

Press release dated Jun. 1, 2010, New York by Keryx Biopharmaceuticals. Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicaiTrials.gov registry, ClinicalTrials Identifier: NCT01097018, data updated Oct. 17, 2011 (ongoing). sponsored by Keryx/AOI Pharmaceuticals, Inc.

"A Phase III Randomized Study to Assess the Efficacy and Safety of Perifosine Plus Capecitabine Versus Placebo II Plus Capecitabine in Patients With Refractory Advanced Colorectal Cancer" recorded in ClinicalTrials.gov registry, ClinicalTrials Identifier: NCT01097018, data updated Oct. 16, 2011 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Jul. 26, 2011 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicaiTrials.gov registry, ClinicalTrials Identifier: NCT01097018, data updated Jul. 19, 2011 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated May 20, 2011 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicaiTrials.gov registry, ClinicalTrials Identifier: NCT01097018, data updated Apr. 18, 2011 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Mar. 7, 2011 (ongoing), sponsored by Keryx/AOI Pharmaceuticals, Inc.

"Phase III Randomized Study to Assess the Efficacy and Safety of Perifosine Plus Capecitabine Versus Placebo Plus Capecitabine in Patients With Refractory Advanced.Colorectal Cancer" recorded in ClinicalTrials.gov registry, ClinicalTrials Identifier: NCT01097018, data updated Feb. 17, 2011 (ongoing). sponsored by Keryx/AOI Pharmaceuticals, Inc.

"A Phase [II Randomized Study to Assess the Efficacy and Safety of Perifosine Plus Capecitabine Versus Placebo Plus Capecitabine in Patients With Refractory Advanced.Colorectal Cancer" recorded in ClinicalTrials.gov registry. ClinicalTrials Identifier: NCT01097018, data updated Jan. 11, 2011 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced.Colorectal Cancer" recorded in ClinicalTrials.gov registry, ClinicalTrials Identifier: NCT01097018, data updated Dec. 15, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced.Colorectal Cancer" recorded in ClinicalTrials.gov registry, ClinicalTrials Identifier: NCT01097018, data updated Nov. 22, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Nov. 4, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Oct. 19, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Sep. 28, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Aug. 27, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Aug. 4, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced.Colorectal Cancer" recorded in ClinicalTrials.gov registry, ClinicalTrials Identifier: NCT01097018, data updated Jul. 16, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Jun. 28, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Jun. 2, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced.Colorectal Cancer" recorded in ClinicalTrials.gov registry, ClinicalTrials Identifier: NCT01097018, data updated May 19, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 27, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 12, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 7, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 2, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced.Colorectal Cancer" recorded in ClinicalTrials.gov registry, ClinicalTrials Identifier: NCT01097018, data updated Apr. 1, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Mar. 31, 2010 (ongoing), sponsored by Keryx/AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Nov. 10, 2011, sponsored by Keryx/AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated May 9, 2011, sponsored by Keryx/AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Oct. 17, 2011, sponsored by Keryx/AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Sep. 22, 2009, sponsored by Keryx/AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov.registry, ClinicalTrials Identifier: NCT00398879, data updated Feb. 16, 2009, sponsored by Keryx/AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Apr. 7, 2008, sponsored by Keryx/AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov.registry, ClinicalTrials Identifier: NCT00398879, data updated Oct. 16, 2007, sponsored by Keryx/AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov.registry, ClinicalTrials Identifier: NCT00398879, data updated Mar. 15, 2007, sponsored by Keryx/AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Feb. 1, 2007, sponsored by Keryx/AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Jan. 31, 2007, sponsored by Keryx/AOI Pharmaceuticals, Inc.

"A Randomized Placebo-Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Nov. 13, 2006, sponsored by Keryx/AOI Pharmaceuticals, Inc.

"A Phase I Study of Perifosine + Capecitabine for Patients With Advanced Colon Cancer" recorded in ClinicalTrials.gov registry, ClinicalTrials Identifier: NCT01048580, dated Nov. 14, 2011.

"A Phase I Study of Perifosine + Capecitabine for Patients With Advanced Colon Cancer" recorded in ClinicalTrials.gov registry, ClinicalTrials Identifier: NCT01048580, dated Oct. 17, 2011.

"A Phase I Study of Perifosine + Capecitabine for Patients With Advanced Colon Cancer" recorded in ClinicalTrials.gov registry, ClinicalTrials Identifier: NCT01048580, dated Jul. 19, 2011.

"A Phase I Study of Perifosine + Capecitabine for Patients With Advanced Colon Cancer" recorded in ClinicalTrials.gov registry, ClinicalTrials Identifier: NCT01048580, dated Mar. 31, 2010.

"A Phase I Study of Perifosine + Capecitabine for Patients With Advanced Colon Cancer" recorded in ClinicalTrials.gov registry, ClinicalTrials Identifier: NCT01048580, dated Jan. 13, 2010.

"A Phase I Study of Perifosine + Capecitabine for Patients With Advanced Colon Cancer" recorded in ClinicalTrials.gov registry, ClinicalTrials Identifier: NCT01048580, dated Jan. 12, 2010.

Argiris et al., A phase II trial of perifosine, an oral alkylphospholipid, in recurrent or metastatic head and neck cancer. Cancer Bioi Ther. Jul. 2006;5( 7): 766-70.

A Wada et al., An EORTC-IDBBC phase I study of gemcitabine and continuous infusion 5-fluorouracil in patients with metastatic breast cancer resistant to anthracyclines or pre-treated with both anthracyclines and taxanes. Eur J Cancer. Apr. 2002;38(6):773-8.

Banker and Rhodes (Eds.), *Modern Pharmaceutics*. 3rd Edition, Revised and Expanded. pp. 451 & 596, Marcel Dekker Inc., ( 1996).

Ghobrial et al. Emerging Drugs in multiple myeloma. Expert Opin. Emerg. Drugs. Mar. 2007; 12(1): 155-63.

Goodman & Gillman. *The Pharmacological Basis of Therapeutic.* 9 Edit pp. 1225-1232 ( 1996).

Hennessy et al., Pharmacod)namic markers of perifosine efficacy. Clin Cancer Res. Dec. 15, 2007; 13(24 ):7421-31.

International Search Report for PCT application No. PCT/US2006/002988 (or PCT publication No. WO 2006/081452) dated Nov. 22, 2007.

International Search Report for PCT application No. PCT/US20 11/030800 (or PCT publication No. WO 20111123691) dated Jul. 25.2011.
Knebel et al.. Quantification of perifosine. An alkylphosphocholine anti-tumour agent. in plasma by pneumatically assisted electrospray tandem mass spectrometry coupled with high-performance liquid chromatography. $J_1$ Chromatogr B Biomed Sci Appl. Jan. 1999 22:721(2):257-69.
Posadas et al., A phase II study of perifosine in androgen independent prostate cancer. Cancer Biol Ther. Oct. 2005:4(10):1133-7.
Press release dated May 31. 2009, New York by Keryx Biopharmaceuticals. Inc.
Ruiter et al. Submicromolar doses of alkylphospholipids induce rapid internalization, but not activation, of epidermal growth factor receptor and concomitant MAPK?ERK activation in A431 cells. Int. J. Cancer. Dec. 2002; 102(4):343-50.
Wolff M.E. (Ed.) "Burger ·s .Medicinal Chemistry .And Drug Discovery"5thEdition, vol. I: Principles and Practice. pp. 975-977, John Wile & Sons. Inc. (1995).
Written Opinion for PCT application No. PCT/US2006/002988 (or PCT publication No. WO 2006:081452), dated Sep. 25, 2007.
Written Opinion for PCT application No. PCT/US2011/030800 (or PCT publication No. WO 2011/123691), dated Jul. 25, 2011.
Bendel eta/., "Randomized Placebo-Controlled Phase II Trial of Perifosine Plus Capecitabine as Second- or Third-Line Therapy in Patients With Metastatic Colorectal Cancer," *J. Clin. Oneal*. (2011), http://jco.ascopubs.org/cgi/doi/1 0.1200/JC0.20 11.36.1980, 8 pages.
Richardson eta/., "Perifosine Plus Bortezomib and Dexamethasone in Patients with.Relapsed/Refractory Multiple Myeloma Previously Treated with Bortezomib: Results of a Multicenter Phase I/II Trial," *J. Clin. Oneal*. (2011), http://jco.ascopubs.org/cgi/doi/1 0.1200/JC0. 201 0.33.9788, 11 pages.
Phase II Study of Perifosine for Patients With Metastatic Carcinoma of the Kidney Who Have Progressed on a VEGF Receptor Inhibitor recorded in ClinicalTrials.gov registry, ClinicalTrials Identifier: NCT00498966, data updated Jul. 10, 2007 (ongoing), sponsored by AOI Pharma, Inc.
A Phase II Trial of Perifosine Following Tyrosine Kinase Inhibitor Failure in Patients With Advanced Renal Cell Carcinoma recorded in ClinicalTrials.gov registry, ClinicalTrials Identifier: NCT00448721, data updated Mar. 16, 2007, (ongoing), sponsored by AOI Pharma, Inc.
A Phase II Trial of Perifosine Following Tyrosine Kinase Inhibitor Failure in Patients With Advanced Renal Cell Carcinoma recorded in ClinicalTrials.gov registry, ClinicalTrials Identifier: NCT00448721, data updated Oct. 29, 2007, (ongoing), sponsored by AOI Pharma, Inc.
Phase I Trial of the Combination of Perifosine and Gemcitabine recorded in.ClinicalTrials.gov registry, ClinicalTrials Identifier: NCT00398697, data updated Nov. 13, 2006, (ongoing), sponsored by AEterna Zentaris.
Phase 1 Trial of the Combination of Perifosine and Gemcitabine recorded in ClinicalTrials.gov registry, ClinicalTrials Identifier: NCT00398697, data updated Jan. 31, 2007, (ongoing), sponsored by AEterna Zentaris.
Phase 1 Trial of the Combination of Perifosine and Gemcitabine recorded in ClinicalTrials.gov registry, ClinicalTrials Identifier: NCT00398697, data updated Aug. 9, 2012, (ongoing), sponsored by AEterna Zentaris.
An Open Label Trial of Perifosine in Patients Currently Being Treated on Perifosine Trials in Solid Tumors or Multiple Myeloma recorded in ClinicalTrials.gov registry, ClinicalTrials Identifier: NCT00847366, data updated Feruary 18, 2009, (ongoing), sponsored by AOI Pharma, Inc.
An Open-Label Phase II Study of the Safety and Efficacy of Perifosine Alone and in Combination With Dexamethasone for Patients With Relapsed or Relapsed/Refractory Multiple Myeloma recorded in ClinicalTrials.gov registry, ClinicalTrials Identifier: NCT00375791, data updated Sep. 12, 2006, (ongoing), sponsored by AOI Pharma, Inc.
An Open-Label Phase II Study of the Safety and Efficacy of Perifosine Alone and in Combination With Dexamethasone for Patients With Relapsed or Relapsed/Refractory Multiple Myeloma recorded in ClinicalTrials.gov registry, ClinicalTrials Identifier: NCT00375791, data updated Nov. 8, 2006, (ongoing), sponsored by AOI Pharma, Inc.
An Open-Label Phase I/II Study of the Safety and Efficacy of Perifosine and Bortezomib With or Without Dexamethasone for Patients With Relapsed or Refractory Multiple Myeloma Previously Treated With Bortezomib recorded in ClinicalTrials.gov registry, ClinicalTrials Identifier: NCT00401011, data updated Nov. 16, 2006, (ongoing), sponsored by AOI Pharma, Inc.
An Open-Label Phase I/II Study of the Safety and Efficacy of Perifosine and Bortezomib With or Without Dexamethasone for Patients With Relapsed or Refractory Multiple Myeloma Previously Treated With Bortezomib recorded in ClinicalTrials.gov registry, ClinicalTrials Identifier: NCT00401011, data updated Dec. 15, 2008 (ongoing), sponsored by AOI Pharma, Inc.
A Phase III Randomized Study to Assessing Perifosine Added to the Combination of Bortezomib and Dexamethasone in Multiple Myeloma Patients recorded in ClinicalTrials.gov registry, ClinicalTrials Identifier: NCT01002248, data updated Oct. 26, 2009 (ongoing), sponsored by AOI Pharma, Inc.
A Phase III Randomized Study to Assessing Perifosine Added to the Combination of Bortezomib and Dexamethasone in Multiple Myeloma Patients recorded in ClinicalTrials.gov registry, ClinicalTrials Identifier: NCT01002248, data updated Oct. 29, 2009 (ongoing), sponsored by AOI Pharma, Inc.
An Open-Label Phase I Study of the Safety of Perifosine in Combination With Lenalidomide and Dexamethasone for Patients With Relapsed or Refractory Multiple Myeloma recorded in ClinicalTrials.gov registry, ClinicalTrials Identifier: NCT00415064, data updated Dec. 21, 2006, (ongoing), sponsored by AOI Pharma, Inc.
An Open-Label Phase I Study of the Safety of Perifosine in Combination With Lenalidomide and Dexamethasone for Patients With Relapsed or Refractory Multiple Myeloma recorded in ClinicalTrials.gov registry, ClinicalTrials Identifier: NCT00415064, data updated Feb. 18, 2009, (ongoing), sponsored by AOI Pharma, Inc.
Gills, Joell, et al., Perifosine: Update on a Novel Akt Inhibitor, Current Oncology Reports-Evolving Therapies, 2009, 11:102-110.
Kondapaka, Sudhir B., Perifosine, A Novel Alkylphospholipid, Inhibits Protein Kinase B Activation, Molecular Cancer Therapeutics, 2003, 1093-1103.
Australian Search Report dated Oct. 30, 2007.
International Search Report dated Jul. 29, 2003.
Paulo Hoff, et al., Subset Analysis of 5-FU Refractory Patients From the Final Results of a Randomized Phase II Study of Perifosine in Combination With Capecitabine (P-Cap) vs. Placebo Plus Capecitabine (Cap) in Patients With Second or Third Line Metastatic Colorectal Cancer (mCRC), 12th World Congress on Gastrointestinal Cancer, Barcelona, Spain, Jun. 30-Jul. 2, 2010.
Sasha Vukelja, et al., Randomized Phase II Study of Perifosine in Combination With Capecitabine vs. Capecitabine Alone in Patients With Second or Third Line Metastatic Colon Cancer, 2009 ASCO Meeting, May 29-Jun. 2, 2009.
Donald Richards, et al., Final Results of a Randomized Phase II Study of Perifosine in Combination With Capecitabine (P-Cap) vs. Placebo Plus Capecitabine (Cap) in Patients With Second or Third Line Metastatic Colorectal Cancer (mCRC), 2010 ASCO Meeting, Jun. 4-8, 2010.
Johanna Bendell, et al., Randomized Phase II Study of Perifosine in Combination With Capecitabine (P-Cap) vs. Placebo Plus Capecitabine (Cap) in Patients with Second or Third Line Metastatic Colon Cancer (mCRC): Updated Results, 2010 ASCO, Gastrointestinal Cancers Symposium. Jan. 24, 2010.
Johanna Bendell, et al., Randomized Placebo-Controlled Phase II Trial of Perifosine Plus Capecitabine As Second- or Third-Line Therapy in Patients With Metastatic Colorectal Cancer Oct. 3, 2011.
F. Anthony Greco, et al., Safety and pharmacokinetic (PK) study of perifosine plus capecitabine (P-CAP) in patients (pts) with refractory metastatic colorectal cancer (mCRC) J Clin Oncol 28, 2010 (suppl; abstr e14086) (2010).

May 31, 2009, Keryx Press Release.
Jun. 1, Keryx Press Release.
Jan. 21, 2010, Keryx Press Release.
Jan. 25, 2010, Keryx Press Release.

Feb. 3, 2010, Keryx Press Release.
Apr. 8, 2010, Keryx Press Release.

* cited by examiner

USE OF ALKYLPHOSPHOCHOLINES IN COMBINATION WITH ANTIMETABOLITES FOR THE TREATMENT OF BENIGN AND MALIGNANT ONCOSES IN HUMANS AND MAMMALS

CROSS-REFERENCE TO RELATED APPLICATIONS

This application is a continuation-in-part (CIP) of U.S. patent application Ser. No. 10/632,187, filed on Jul. 30, 2003, which claims the benefit of U.S. Provisional Application No. 60/399,615, filed Jul. 30, 2002, which is hereby incorporated by reference.

BACKGROUND OF THE INVENTION

Alkylphosphocholines are a new class of organic compounds, which exhibit diversified anti-neoplastic activities (M. Lohmeyer and R. Bittman, Antitumor Ether Lipids and Alkylphosphocholines, DOF, 19 (11), 1021-1037 (1994)). The effect of the alkylphosphocholines in this connection may be based on different, molecular and biochemical mechanisms, some of which take place on the level of the plasma membrane of the cell.

It is well known that alkylphosphocholines influence inositol metabolism, the interaction with phospholipases or inhibition of protein kinase C and thus that this class of substances has a general influence on cellular signal transduction (K. Maly et al., Interference of New Alkylphospholipid Analogues With Mitogenic Signal Transduction, Anti-Cancer Drug Design, 10, 411-425 (1995); and P. Hilgard, et al., D21266, A New Heterocyclic Alkylphospholipid with Antitumor Activity, Eur. J. Cancer, 33 (3), 442-446 (1997)). Thus, the alkylphosphocholine perifosine shows growth-inhibitory properties in relation to various melanoma, CNS, lung, colon, prostate and breast cancer cell lines with an $IC_{50}$ ranging from 0.2 to 20 μM.

It is further known that perifosine blocks tumor cells in the $G_1$-S and $G_2$-M phase of the cell cycle (V. Patel, et al., A Novel Alkylphospholipid, Induces p. 21$^{Waf1}$ Expression in Squamous Carcinoma Cells through a p53-independent Pathway, Leading to Loss in Cyclindependent Kinase Activity and Cell Cycle Arrest, Cancer Research 62, 1401-1409 (2002)).

It is known that the use of alkylphosphocholines before or together with radiation therapy leads its synergistic effects during the treatment of tumors (P. Principe et al., Evaluation of Combinations of Antineoplastic Ether Phospholipids and Chemotherapeutic Drugs, Anti-Cancer Drugs, 3 (6), 577-587 (1992)). It has also been reported that different glycerol-3-phospholipids, such as ET-18-OOCH$_3$, in combination with different DNA-interacting substances or tubulin binders increase the anti-tumor activity in vitro in a different tumor cell lines (P. Principe et al., Synergistic Cytotoxic Effect of Aza-alkylphospholipids in Association with Chemotherapeutic Drugs, J. Lipid Mediators Cell Signalling, 10 (1-2), 171-173 (1994)).

Despite advances in the treatment of cancer using perifosine and a variety of other antitumor agents, there still exists a need in developing more effective therapies for the treatment of a variety of different types of cancer. Certain types of cancers, such as multiple myeloma, renal cancer, breast cancer and colon cancer have proved to be particularly difficult to control. Thus, an effective means of treating these cancers that prolong the survival rate of patients without causing serious side effects would be a considerable advance.

BRIEF SUMMARY OF THE INVENTION

Surprisingly, it has been found that administering specific combinations of an alkylphosphocholine and an antimetabolite show a synergistic effect towards the treatment of multiple myeloma, breast cancer, colon cancer and renal cancer. The combination therapy allows for the use of lower doses of the individual antitumor agents and thus is less toxic to the patient.

One aspect of the present invention involves a method of treating multiple myeloma, colon, breast or renal cancer using a combination of an alkylphosphocholine and an antimetabolite.

Another aspect of the present invent involves a method of treating multiple myeloma, breast, colon or renal cancer comprising administering a therapeutically effective amount of perifosine or miltefosine and a therapeutically effective amount of an antimetabolite.

Still another aspect of the present invention involves a method of treating multiple myeloma, colon, breast or renal cancer comprising administering a therapeutically effective amount of perifosine and a therapeutically amount of capecitabine.

DETAILED DESCRIPTION OF THE INVENTION

The present invention provides a novel use of linear alkylphosphocholines of the general Formulas I and II in an inventive combination with other medicinal drugs for the treatment of multiple myeloma, renal cancer or colon cancer. According to one aspect of the invention, the compounds of the general Formulas I and II can be used in an inventive combination with an antimetabolite. The alkylphosphocholines of the general Formulas I and II, on which the invention is based, may be used in the form of finished medicinal drugs. The compounds, on which the invention is based, are described by the general Formulas I and II:

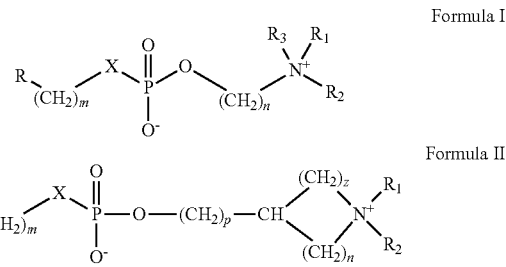

in which, independently of one another,
n, m, p, z is a whole number between 0 and 4,
X is O, S, NH;
R is hydrogen, a linear or branched $C_1$ to $C_{20}$ alkyl group, which may be saturated or unsaturated with one to three double and/or triple bonds and unsubstituted or optionally substituted at the same or at different carbon atoms with one, two or more halogen, nitro, cyano, hydroxy, $C_1$ to $C_6$ alkoxy, amino, mono-($C_1$ to $C_4$) alkylamino or di-($C_1$ to $C_4$) alkylamino groups,
$R_1$, $R_2$, $R_3$ independently of one another represent hydrogen, a linear or branched ($C_1$ to $C_6$) alkyl group, preferably methyl and ethyl, a ($C_3$ to CO cyclo alkyl group, which may be unsubstituted or optionally substituted at the same or different carbon atoms with one, two or more halogen, nitro, cyano, hydroxy, $C_1$ to $C_6$ alkoxy, amino, mono-($C_1$ to $C_4$) alkylamino or di-($C_1$ to $C_4$) alkylamino groups.

As used herein, multiple myeloma refers to cancer of the white blood cells (or plasma). As used herein, breast cancer refers to any cancer originating in the breast tissue including carcinomas and adenocarcinomas. As used herein colon cancer refers to any cancer originating in the colon, including all types of colon and colorectal adenocarcinoma and carcinoma. As used herein, renal cancer refers to any cancer that originates in the kidney, including, but not limited to, renal cell carcinoma, renal cell adenocarcinoma, clear cell carcinoma, renal pelvis carcinoma, squamous cell carcinoma, juxtaglomerular cell tumor (reninoma), angiomyolipoma, renal oncocytoma, Bellini duct carcinoma, clear-cell sarcoma of the kidney, mesoblastic nephroma, Wilms' tumor, and mixed epithelial stromal tumor.

According to one aspect of the invention, a method for controlling multiple myeloma, renal cancer, breast cancer or colon cancer in humans and in mammals is provided and comprises administering at least one of the compounds of the general Formula I and II on which the invention is based to the human or a mammal in an amount effective for tumor treatment before or during a treatment with an antimetabolite.

The therapeutically effective dose, to be administered for the treatment, of the particular compound of the general formula I and II on which the invention is based depends inter alia on the nature and the stage of the oncosis, the age and sex of the patient, the mode of administration and the duration of treatment. The compounds on which the invention are based can be administered in a drug product as liquid, semisolid and solid drug forms. This takes place in the manner suitable in each case in the form of aerosols, oral powders, dusting powders and epipastics, uncoated tablets, coated tablets, emulsions, foams, solutions, suspensions, gels, ointments, pastes, pills, pastilles, capsules or suppositories.

In one embodiment, the present invention provides a method of treating multiple myeloma, renal cancer, breast cancer or colon cancer by administering an alkylphosphocholine of the Formulas I or II before and/or during administration of at least one antimetabolite. Preferred alkylphosphocholines used in accordance with the present invention include perifosine (octadecyl 1,1-dimethylpiperidinium-4-yl phosphate) and miltefosine. A particularly preferred alkylphosphocholines is perifosine. Preferred antimetabolites include but are not limited to 5-azacytidine, 2-mercaptopurine, 5-fluorouracil, 6-thioguanine, capecitabine, cladribine, clofarabine, cytarabine, decitabine, doxifluridine, floxuridine, fludarabine, forodesine, gemcitabine, nelarabine, pentostatin, sapacitabine, thiarabine or Troxacitabine. A particularly preferred antimetabolite is capecitabine.

In one preferred embodiment, a therapeutically effective amount of perifosine in combination with a therapeutically effective amount of 5-flurouracil or a prodrug of 5-flurouracil is administered to a patient with multiple myeloma, colon cancer or renal cancer. A preferred prodrug of 5-flurouracil is capecitabine. The amount of perifosine may range from about 20 mg/day to about 100 mg/day. The amount of capecitabine may range from about 500 mg/m² to about 2500 mg/m² daily.

In another preferred embodiment, a therapeutically effective amount of miltefosine in combination with a therapeutically effective amount of 5-flurouracil or a prodrug of 5-flurouracil is administered to a patient with multiple myeloma, colon cancer or renal cancer. A preferred prodrug of 5-flurouracil is capecitabine. The amount of miltefosine may range from about 20 mg/day to about 100 mg/day. The amount of capecitabine may range from about 500 mg/m² to about 2500 mg/m² daily.

The invention claimed is:

1. A method of treating multiple myeloma, wherein the method comprises administering a therapeutically effective amount of an alkylphosphocholine compound having the structure of Formula II:

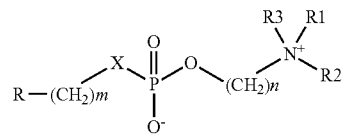

in which, independently of one another:
m, n, p, z are a whole number between 0 and 4;
X is O;
R is H, a straight-chain or branched ($C_1$-$C_{17}$)-alkyl group which may be saturated or unsaturated with one or two double and/or triple bonds;
$R_1$, $R_2$ are, independently of one another, H or a straight-chain or branched ($C_1$-$C_6$)-alkyl group, preferably methyl and ethyl, a ($C_3$-$C_7$)-cycloalkyl group,
wherein said alkylphosphocholine is administered before and/or during treatment with at least one antimetabolite selected from the group consisting of 5-Azacytidine, 2-Mercaptopurine, 5-fluorouracil, 6-Thioguanine, Capecitabine, Cladribine, Clofarabine, Cytarabine, Decitabine, Doxifluridine, Floxuridine, Fludarabine, Forodesine, Gemcitabine, Nelarabine, Pentostatin, Sapacitabine, Thiarabine and Troxacitabine.

2. The method according to claim 1, wherein said alkylphosphocholine is octadecyl 1,1-dimethylpiperidinium-4-yl phosphate (perifosine).

3. The method according to claim 1, wherein said method comprises administering a pharmaceutical composition comprising a therapeutically effective amount of an alkylphosphocholine compound of the general Formula II, customary pharmaceutical carriers, excipients and/or diluents, and wherein said composition is administered before and/or during the treatment with at least one antimetabolite.

4. The method according to claim 1, wherein said alkylphosphocholine is administered before and/or during treatment with two or more antimetabolites.

5. The method according to claim 1, wherein said alkylphosphocholine is octadecyl 1,1-dimethylpiperidinium-4-yl phosphate (perifosine) and said antimetabolite is capecitabine.

6. A method of treating colon cancer, wherein the method comprises administering a therapeutically effective amount of an alkylphosphocholine compound having the structure of Formula II:

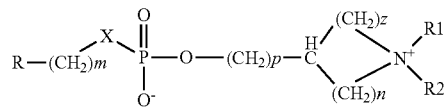

in which, independently of one another:
m, n, p, z are a whole number between 0 and 4;
X is O;

R is H, a straight-chain or branched (C1-C17)-alkyl group which may be saturated or unsaturated with one or two double and/or triple bonds;

R1, R2 are, independently of one another, H or a straight-chain or branched (C1-C6)-alkyl group, preferably methyl and ethyl, a (C3-C7)-cycloalkyl group, wherein said alkylphosphocholine is administered before and/or during treatment with at least one antimetabolite selected from the group consisting of 5-Azacytidine, 2-Mercaptopurine, 5-fluorouracil, 6-Thioguanine, Cladribine, Clofarabine, Cytarabine, Decitabine, Doxifluridine, Floxuridine, Fludarabine, Forodesine, Gemcitabine, Nelarabine, Pentostatin, Sapacitabine, Thiarabine and Troxacitabine.

7. The method according to claim 6, wherein said alkylphosphocholine is octadecyl 1,1-dimethylpiperidinium-4-yl phosphate (perifosine).

8. The method according to claim 6, wherein said method comprises administering a pharmaceutical composition comprising a therapeutically effective amount of an alkylphosphocholine compound of the general Formula II, customary pharmaceutical carriers, excipients and/or diluents, and wherein said composition is administered before and/or during the treatment with at least one antimetabolite.

9. The method according to claim 6, wherein said alkylphosphocholine is administered before and/or during treatment with two or more antimetabolites.

\* \* \* \* \*